United States Patent

Piety et al.

[11] Patent Number: 5,965,819
[45] Date of Patent: Oct. 12, 1999

[54] PARALLEL PROCESSING IN A VIBRATION ANALYZER

[75] Inventors: Kenneth R. Piety; James C. Robinson; Thomas E. Nelson, all of Knoxville, Tenn.

[73] Assignee: CSI Technology, Wilmington, Del.

[21] Appl. No.: 09/110,807

[22] Filed: Jul. 6, 1998

[51] Int. Cl.⁶ ............................... G01N 29/00; H03F 1/26
[52] U.S. Cl. ................................ 73/660; 73/602; 702/56; 702/77
[58] Field of Search ............................. 73/660, 661, 659, 73/40.7, 587, 657, 602; 702/56, 76, 77, 38, 57, 58, 59, 104, 185, 190

[56] References Cited

U.S. PATENT DOCUMENTS

| | | | |
|---|---|---|---|
| 3,705,516 | 12/1972 | Reis | 73/71.4 |
| 3,883,803 | 5/1975 | Donald et al. | 324/77 K |
| 4,056,725 | 11/1977 | Kamburov et al. | 250/336 |
| 4,477,190 | 10/1984 | Liston et al. | 356/418 |
| 4,507,740 | 3/1985 | Star et al. | 364/487 |
| 4,685,065 | 8/1987 | Braun et al. | 364/485 |
| 4,928,246 | 5/1990 | Crawley et al. | 364/514 |
| 4,991,105 | 2/1991 | Pimental | 364/483 |
| 5,005,946 | 4/1991 | Brandstetter | 350/162.12 |
| 5,008,841 | 4/1991 | McElroy | 364/551.01 |
| 5,068,813 | 11/1991 | Thoen | 364/572 |
| 5,122,732 | 6/1992 | Engeler et al. | 324/77 E |
| 5,340,990 | 8/1994 | Brackenbush et al. | 250/395 |
| 5,390,545 | 2/1995 | Doan | 73/650 |
| 5,410,621 | 4/1995 | Hyatt | 382/69 |
| 5,445,028 | 8/1995 | Bianchi et al. | 73/593 |
| 5,526,286 | 6/1996 | Sauerwein et al. | 364/550 |
| 5,566,092 | 10/1996 | Wang et al. | 364/551.02 |
| 5,633,811 | 5/1997 | Canada et al. | 364/576 |

*Primary Examiner*—Hezron Williams
*Assistant Examiner*—Helen C. Kwok
*Attorney, Agent, or Firm*—Luedeka, Neely & Graham, PC

[57] ABSTRACT

A portable data collector and analyzer having multiple paths for performing multiple processing functions on a single sensor signal in parallel. The portable data collector has a sensor which creates a sensor signal that represents a measured property of an operating machine. The sensor signal is simultaneously sent to at least two processor channels that are connected in parallel. Each processor is capable of performing different types of signal analysis with varying signal conditioning and sampling rate requirements on the sensor signal independent of the other processor(s). An operator of the parallel processing data collector and analyzer places the single sensor on the area desired to be tested and instructs the parallel processing data collector to begin taking measurements. The parallel processor channels work independently of each other to obtain results corresponding to a number of different tests in approximately the time normally required to perform a single test.

21 Claims, 4 Drawing Sheets

PARALLEL PROCESSING IN A VIBRATION ANALYZER

FIELD OF THE INVENTION

In general, the present invention relates to a portable data collector and analyzer for monitoring operating machinery and detecting machine fault conditions. In particular, the present invention relates to a portable data collector and analyzer that uses parallel processors to simultaneously perform measurement functions on an electrical signal from a single sensor.

BACKGROUND OF THE INVENTION

Defects in operating machines often result in the machine producing increased vibrations at certain frequencies. For example, a rotating gear with a cracked tooth will produce an increased amount of vibration every time the cracked tooth comes into contact with an associated gear. It is well known that these vibrations tend to be detectable long before the machinery defect becomes serious enough to cause the machine to malfunction. Therefore, vibrations produced by operating machines are measured in order to detect machinery defects before they cause a failure.

Typically, vibration data collectors and analyzers are used to take vibration measurements from operating machines and analyze the vibration measurements to determine if a machinery defect is likely to be present. The process of performing periodic predictive maintenance surveys on plant equipment is a manual process that involves a technician carrying a vibration analyzer to each measurement point and affixing a probe to the measurement point to measure vibration data and other types of dynamic signals and process variables. This process often involves anywhere from ten seconds to several minutes at each measurement location. Because industrial plants often have large amounts of machinery, performing these measurements becomes a time consuming task. In a single 8-hour shift, a technician could spend no more than 30 seconds for each measurement if his total measurement route included 1000 locations. Thus, in order to cover large populations of equipment in a cost effective manner, there is a need to minimize the amount of time spent at each measurement location. However, this need to minimize the amount of time spent collecting data is at odds with the need to get the full complement of measurements required to provide optimal detection and diagnosis of machine faults. To reliably detect machinery faults, it is often desirable to measure several parameters such as an overall vibration reading, multiple vibration spectra with differing engineering units and/or band widths, and a vibration spectrum produced by an enveloping process. These and other measurements may be needed at any given measurement location in order to detect the fault modes characteristic to the machinery being monitored. These multiple measurements impose a heavy time burden on the technician performing the measurements.

Analyzers with two or more parallel processing channels have been available for some time. One such prior art device is the CSI 2120 analyzer which is described in U.S. Pat. No. 5,633,811. In general, these types of portable analyzers were introduced to enable a technician to take measurements from several sensors simultaneously. Typically, the independent sensors are positioned with different spatial orientations with respect to the machine being monitored, such as horizontally, vertically, and axially. Each sensor has an associated processing channel that processes the signal produced by it. This approach may reduce the amount of time required to collect a set of measurements if the analyzer has been designed with sufficient processing power. However, the disadvantage of this approach is that the technician performing the tests has to manage the task of handling multiple sensors and insuring that the correct sensor is in the correct measurement location. Insuring proper sensor placement involves a considerable amount of time and effort and, thus, minimizes the time savings realized from using multiple sensors with multiple processing paths. In addition, the likelihood of taking an erroneous measurement is significantly increased by the increased complexity.

SUMMARY OF THE INVENTION

The intention of this patent is to provide a new device that reduces the amount of time required to perform periodic maintenance surveys on operating machinery. The present invention accomplishes this goal by providing a portable multi-channel signal analyzer that utilizes multiple data acquisition and analysis channels connected in parallel but having the capability of processing a single sensor signal. The ability to process the same sensor signal in parallel on multiple paths with different type measurements improves the speed and does not introduce the complexity of handling (or mishandling) multiple sensors.

The invention consists of a hand held data collector and analyzer for collecting, analyzing and storing data relating to the operational characteristics of a machine. For example, vibrations are produced by operating machinery and are often indicative of the condition of the machinery. The device of a preferred embodiment has a sensor that is placed against the vibrating machine. A vibration transducer in the sensor senses the vibrations produced by the machine and produces an analog signal that corresponds to the vibrations. The analog signal is received and conditioned by first and second conditioning circuits that produce first and second conditioned analog signals. These conditioning circuits also contain analog to digital converters that sample the conditioned analog signals to produce first and second digital signals. Depending upon the processed outputs to be calculated, the analog to digital converters may sample the conditioned analog signals at different sampling rates. The first and second digital signals are respectively received by first and second data processors that process the digital signals to produce a set of desired digital data. For example, the digital data set may include data such as a frequency spectrum produced by performing a Fast Fourier Transform on the signal. This frequency spectrum can be examined to determine the absence or presence of machine defects. The data processors are interfaced with a memory that stores the digital data set for later retrieval and analysis. In an especially preferred embodiment, a central processing unit is used to control and harmonize the functioning of the data processors. The central processing unit and the data processors are electrically interfaced with a keyboard that allows a user of the vibration collecting and analyzing device to input commands and data. In addition, the central processing unit uses a display to provide the user information concerning the status and results of the measurements.

While the preferred embodiment is described herein in connection with vibration, other embodiments of the invention measure other operational parameters of machines such as for example, but without limitation, voltage, current, flux, temperature, pressure, force, speed, displacement, energy, color, frequency, etc.

Processing the signal in parallel results in a substantial time savings over the prior art approach of calculating each measurement function in a sequential manner. Because the separate microprocessors operate in parallel to analyze signals from the same sensor and perform the calculations necessary to obtain the different processed outputs or analyses that are helpful in detecting machinery defects, the time required to calculate a set of desired processed outputs or perform desired analysis is drastically reduced. In addition, the independent parallel processing paths allow the multichannel analyzer to process the same sensor signal with different signal conditioning and sampling rates simultaneously. This allows the optimum signal conditioning and sampling rate for a particular type of processed output or analysis to be implemented. Thus, the accuracy and reliability of measurements can also be increased. Furthermore, a set of processed outputs calculated contemporaneously with one another may sometimes be more beneficial than a set of processed outputs calculated at different points in time. For example, knowing the acceleration time waveform and the velocity time waveform received from an operating machine during the same particular range in time may be more useful than knowing the acceleration waveform received during one range in time and the velocity waveform received during another range in time.

Thus, the present invention significantly reduces the amount of time required to obtain a given amount of data without increasing the complexity of the measurement taking process. This results in significant savings in the labor costs associated with data gathering and a dramatic increase in the amount of data collected and the corresponding ability to detect machinery faults. Yet other objects, features and advantages of the vibration collecting and analyzing device will become apparent by reference to the following detailed description.

BRIEF DESCRIPTION OF THE DRAWINGS

The present invention can be better understood by reference to the drawings below wherein like reference characters refer to like parts throughout the several views, and wherein.

DESCRIPTION OF THE PREFERRED EMBODIMENT(S)

Figure 1:
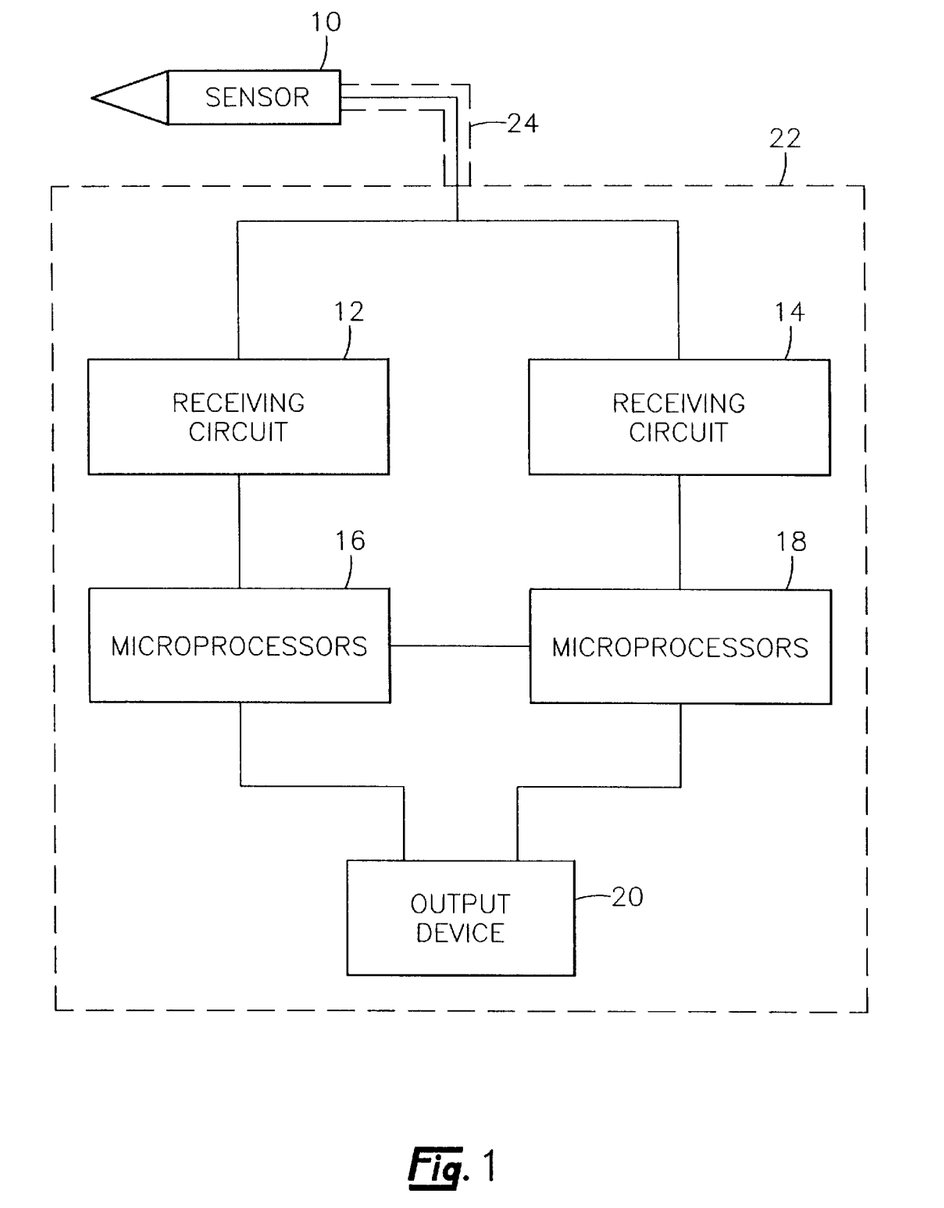
FIG. 1 is a block diagram of a data collector and analyzer having parallel processors connected to the same sensor.

The data collecting and analyzing system of the present invention effectively reduces the amount of time necessary to collect a given amount of data from a sensor without increasing the complexity of the measurement taking process. These benefits are realized by providing a sensor output to at least two microprocessors that are operating independently of one another. This situation is depicted in FIG. 1.

The operating condition of a machine can often be diagnosed by examining the vibrations produced by it when it is operating. Thus, the data collecting and analyzing device has a sensor 10 that produces an electrical signal in response to a vibration. By placing the sensor 10, in contact with the machine, an electrical signal is generated that corresponds to the vibrations produced by the machine. The output of the sensor 10 is electrically connected to a pair of receiving circuits 12 and 14. The receiving circuits 12 and 14 receive and condition the electrical signal produced by the sensor 10. By conditioning the electrical signal, the receiving circuits 12 and 14 place the electrical signal in a form that is readable by a pair of microprocessors 16 and 18. Furthermore, the provision of two separate receiving circuits 12 and 14 allows the electrical signal to be conditioned differently depending upon its later intended use.

The microprocessors 16 and 18 receive the conditioned electrical signals from the receiving circuits 12 and 14 and independently and simultaneously analyze the signals to produce first and second processed outputs that are indicative of the presence or absence of a machinery defect in the operating machine being monitored. There are a number of known processed outputs that may be indicative of machinery defects. One such processed output is based upon the amount of energy in certain frequency bands of the vibration spectrum produced by the operating machine. By comparing the calculated amount of energy in each frequency band and the deviation of the amount from a set of acceptable values, one of the microprocessors 16 or 18 can calculate a value that represents the operating health of the machine. In addition, machine fault conditions tend to generate vibration peaks at certain frequencies. Peaks occurring at harmonic and sideband frequencies of the operating machine frequencies are often directly related to specific machine fault conditions. Thus, while one of the microprocessors 16 or 18 is calculating and examining the level of the vibration signal in certain frequency bands, the other microprocessor 16 or 18 may be locating the peaks in the vibration spectrum, or it may be performing a Peak Vue® analysis as described in U.S. patent application Ser. No. 08/840,844.

Independently and simultaneously processing and analyzing the electrical signal produced by the sensor 10 significantly reduces the time needed to acquire a given amount of data. If two operations requiring fifteen seconds of processing time each were performed sequentially, a user of the data collector and analyzer would be required to hold the sensor 10 against the operating machine for thirty seconds. However, by performing the operations simultaneously, the user is only required to hold the sensor 10 against the operating machine for fifteen seconds. As the number of measurements taken increases, the time savings realized by the present invention becomes more and more significant.

The processed outputs calculated by the microprocessors 16 and 18 are sent to an output device 20. The output device 20 may be an infrared or RS 232 communications port that allows the data analyzer and collector to communicate with an external device such as a computer. Once the computer receives the processed outputs, the processed outputs may be stored or compared to previous readings taken from the machine to determine if the machines' condition is worsening or remaining constant. In an alternative embodiment, the output device 20 is an liquid crystal display that allows a user of the date collecting and analyzing device to visually determine the status of the operating machine. Microprocessor 16 is preferably programmed as the master processor that controls the overall operation of the instrument and provides control signals to microprocessor 18, which preferably controls the receiving circuit 14 in response to such control signals.

In a preferred embodiment, the electrical components of the data collector and analyzer are contained in a housing 22 that allows the collector and analyzer to be portably carried from one testing location to another. The sensor 10 is attached to the housing 22 by a flexible cord 24 that electrically connects the sensor output to the receiving circuits 12 and 14.

Figure 2:
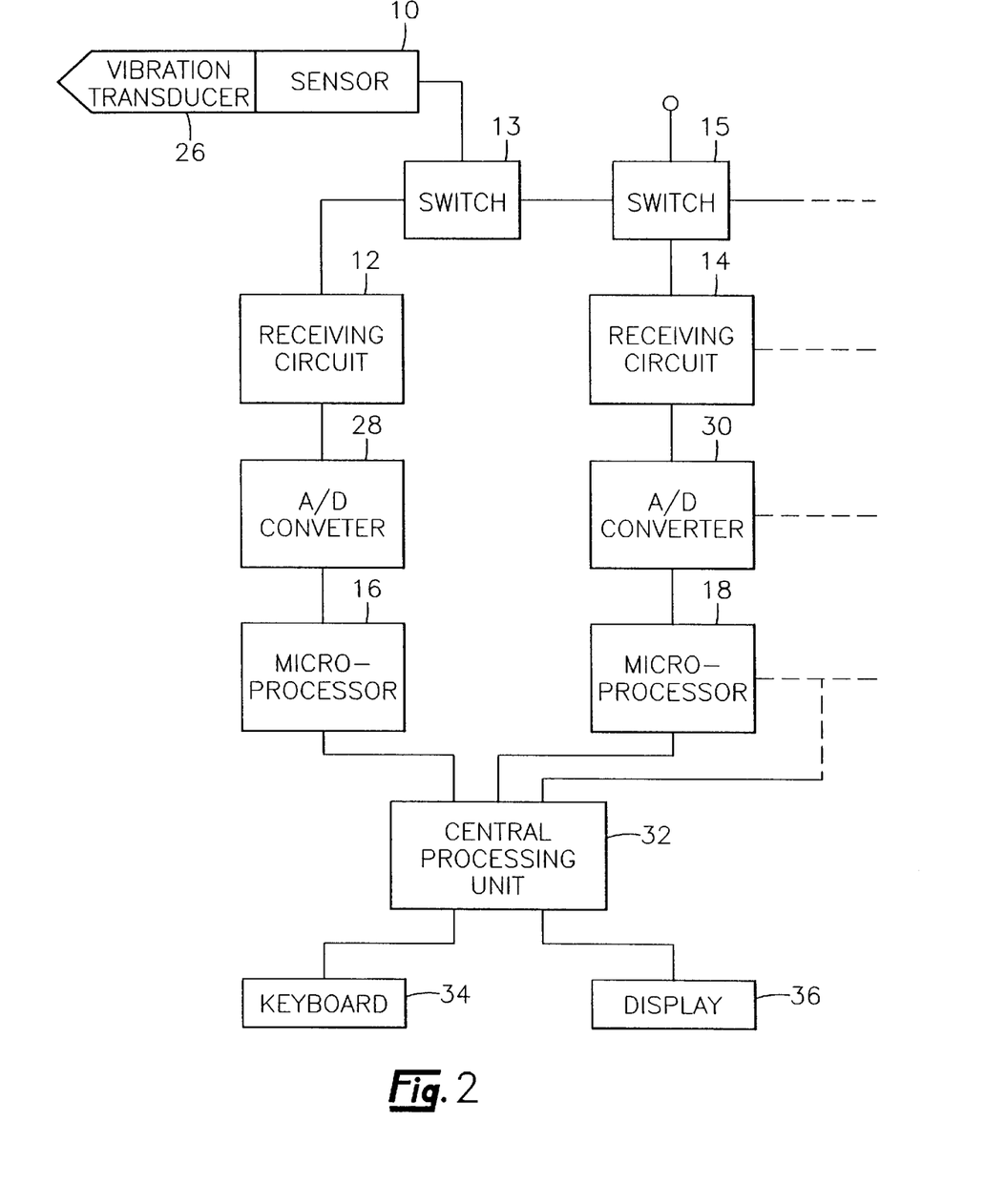
FIG. 2 is a block diagram of a data collector and analyzer having a plurality of parallel processors connected to receive signals from the same sensor and controlled by a central processing unit.

Referring now to FIG. 2, an especially preferred embodiment of the present invention is shown. A vibration transducer 26 contained inside the sensor 10 produces an electrical signal that corresponds to the vibrations detected by the vibration transducer 26. The sensor output is electrically connected to a plurality of receiving circuits 12 and 14. As discussed in more detail below, the receiving circuits 12 and 14 amplify the sensor signal to a desired level and filter the signal to remove any unwanted high or low frequency components. The type and amount of filtering and amplifying employed depends upon the analysis to be performed on the sensor signal. While only two receiving circuits 12 and 14 are shown, it is expressly understood that more than two receiving circuits may be electrically connected in parallel to receive the electrical sensor signal. More parallel channels are employed to increase the number of operations that may be simultaneously performed on the electric sensor signal.

The outputs of the receiving circuits 12 and 14 are electrically connected to a plurality of analog to digital converters 28 and 30. Once more, while only two analog to digital converters 28 and 30 are shown in FIG. 2, it is expressly understood that there may be numerous analog to digital converters. Furthermore, while the output of each receiving circuit 12 and 14 in FIG. 2 is shown as electrically connected to an analog to digital converter 28 and 30, the output of one receiving circuit 28 may be electrically connected to an analog to digital converter 28 while the output of the other receiving circuit 30 is electrically connected directly to a microprocessor 18. However, in the preferred embodiment shown in FIG. 2, the outputs of both receiving circuits 12 and 14 are received by analog to digital converters 28 and 30. Switches 13 and 15 are also operable under control of the CPU 32 to connect the receiving circuits 12 and 14 to different inputs.

The analog to digital converters 28 and 30 sample the conditioned analog signal from the receiving circuits 12 and 14 to produce a digitized output signal that corresponds to the conditioned analog signal. One of the benefits of the parallel processing paths of the present invention is that the analog to digital converters 28 and 30 can be configured to sample the analog signals at different sampling rates. Thus, the particular sampling rate used for each analog to digital converter 28 and 30 depends upon the ideal sampling rate for the particular processed output that will be calculated from the sampled signal.

As shown in FIG. 2, a plurality of microprocessors, including microprocessors 16 and 18, receive the digitized signals from the plurality of analog to digital converters 28 and 30. The microprocessors 16 and 18 perform digital signal analysis techniques on the digitized signals to produce processed outputs of interest. Preferably, a Fast Fourier Transform is performed by at least one of the microprocessors 16 and 18 to produce a frequency spectrum. An overall vibration reading is also a useful processed output that is typically used to diagnose machinery defects.

The plurality of microprocessors are controlled by a central processing unit 32. The central processing unit 32 coordinates the functioning of the microprocessors 16 and 18 by providing them instructions concerning the data collection and analysis such as when to begin processing data, what type of processing to perform, how many values to calculate, etc. The central processing unit 32 receives commands from the user through, for example, a keyboard 34 and displays information to the user on a display 36. The keyboard 34 allows the user to control the functioning of the data collector and analyzer. The display 36 provides information to the user concerning the status and results of the data collecting and analyzing process. The central processing unit 32 also uses the display 36 to prompt the operator of the data collector and analyzer to enter information concerning the data to be collected and analyzed.

Figure 3:
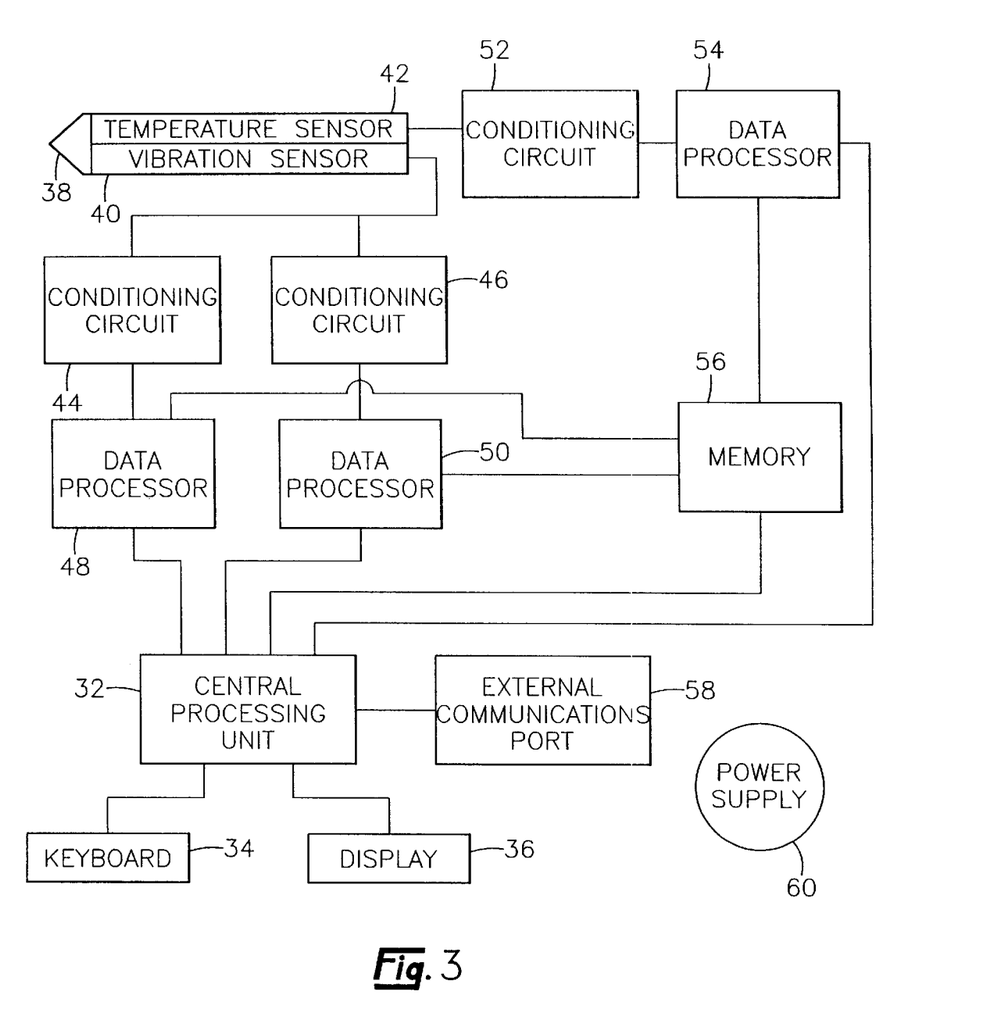
FIG. 3 is a block diagram of a data collector and analyzer with parallel processors and a direct access memory constituting another embodiment of the invention.

Referring now to FIG. 3, yet another embodiment of the present invention is shown. This embodiment uses a single sensor 38 that contains both a vibration sensing element 40 and a temperature sensing element 42. The vibration sensing element 40 produces an electrical vibration signal corresponding to the vibrations of an object. The electrical vibration signal is received by a pair of conditioning circuits 44 and 46. The conditioning circuits 44 and 46 filter and process the electrical vibration signal independently of one another until the electrical vibration signal is in condition to be received by the particular data processor 48 or 50 associated with the conditioning circuit 44 or 46.

The data processors 48 and 50 receive and process the conditioned analog vibration signal to produce a set of desired digital data. In a preferred embodiment, the data processors 48 and 50 contain internal analog to digital converters. The analysis performed by the processors 48 and 50 preferably includes operations such as Fast Fourier Transforms and rasterization functions that allow the frequency spectrum produced by the Fast Fourier Transform to be graphically displayed.

In an alternative embodiment, the data processors 48 and 50 are digital signal processors that perform digital filtering and decimation on the conditioned analog signal received from the conditioning circuits 44 and 46. The digital signal processors have analog to digital converters which are used to digitize the conditioned analog signal. The digital signal processors use digital filtering and decimation to reduce the sample rate and frequency content of the digitized conditioned analog signal.

The temperature sensing element 42 produces an electrical temperature signal that corresponds to the temperature of an object placed in contact with the sensor 38. The electrical temperature signal is received by a conditioning circuit 52 which filters and conditions the electrical temperature signal so that it can be read by the data processor 54. The data processor 54 examines the conditioned temperature signal and produces a digital signal that is representative of the surface temperature of the object placed in contact with the sensor 38.

The three data processors 48, 50 and 54 are controlled by a central processing unit 32. The central processing unit 32 receives the digital outputs from the data processors 48, 50 and 54 and produces output signals that are sent to the display 36 that allow an operator to determine the progress and results of the data processors' 48, 50 and 54 analysis. The central processing unit 32 also provides instructions to the data processors 48, 50 and 54 that identify the data that needs to be stored in the memory 56. In addition, the central processing unit 32 receives input signals from a keyboard 34. The keyboard 34 allows the operator of the data collecting and analyzing system to provide the central processing unit 32 with commands concerning the type, duration, etc. of the measurements to be taken. A power supply 60 provides electrical power to the components of the data collecting and analyzing device. Preferably, the power supply 60 is a rechargeable device that holds enough power to allow the operator to complete a monitoring cycle without having to recharge the power supply 60. In order to simplify FIG. 3 and make it easier to understand, the numerous power supply connections between the power supply 60 and the various elements of the device are not shown.

The data processors 48, 50 and 54 have direct access to the memory 56. Thus, as processed outputs are calculated they can be immediately stored in the memory 56 without having to interrupt the central processing unit 32. When the central processing unit 32 is ready to send the processed outputs to the display 36 or an external communications port 58, the central processing unit accesses the memory 56 and retrieves the desired information. The external communication port 58 allows the data collecting and analyzing device to communicate with external devices such as a main computer. The external communications port 58 is preferably an RS 232 port. However, the external communications port 58 may also be an infrared transceiver, a wireless radio frequency transmitter, or a variety of other similar communications systems.

The data processors 48, 50 and 54 operate independently and simultaneously upon the incoming vibration sensor signal and temperature sensor signal to receive, analyze and store the data without interrupting the central processing unit 32. Thus, the central processing unit 32 is free to perform other control activities as discussed in more detail above. This approach further minimizes the time needed to perform the measurements and greatly increases the overall speed of the data collection and analysis by distributing the computations and control activities between the data processors 48, 50 and 54 and the central processing unit 32. In addition, because the conditioning circuits 44 and 46 and data processors 48 and 50 function independently of one another, different sampling rates and filtering techniques may be applied to the same signal simultaneously. Furthermore, the data processors 48, 50 and 54 may have different processing capabilities depending upon the processing power needed to calculate the particular processed output assigned to the particular data processor 48, 50 or 54.

Figure 4:
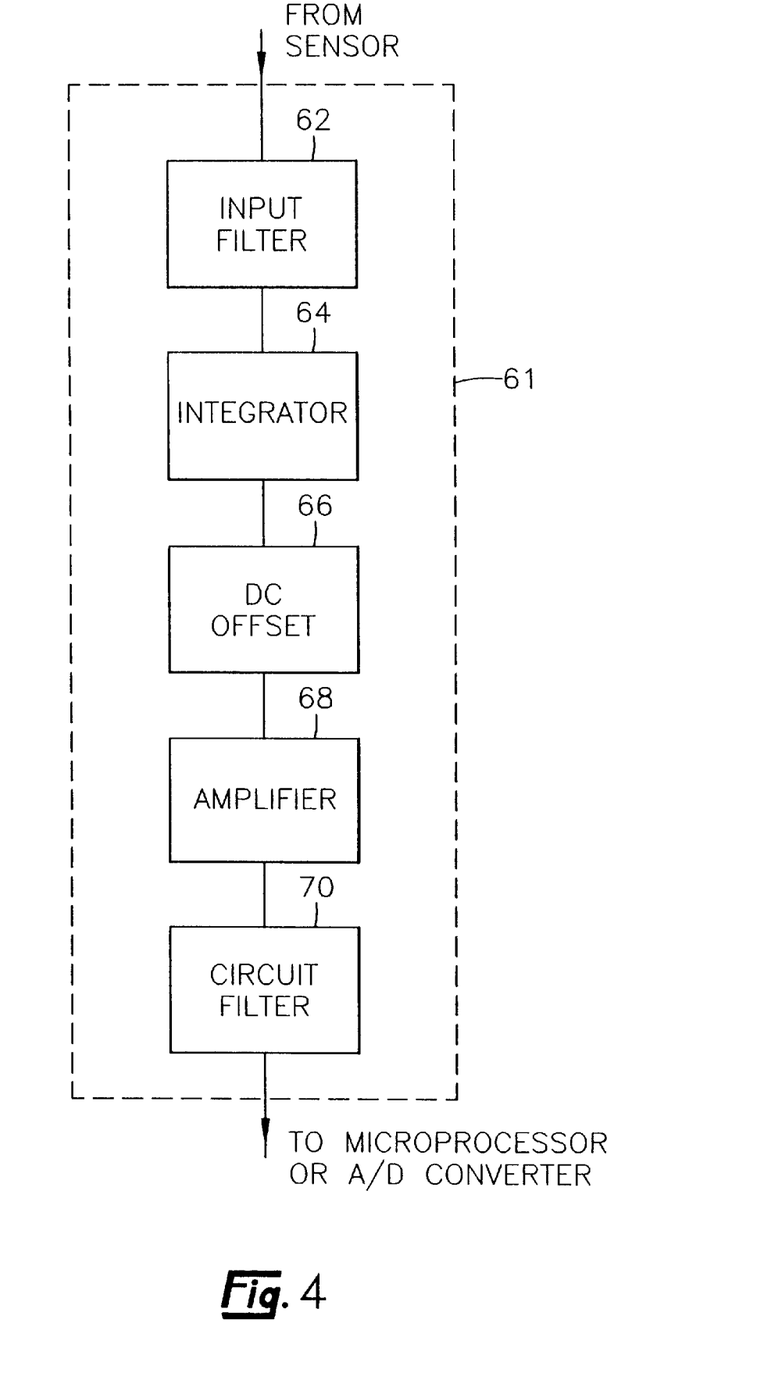
FIG. 4 is a block diagram of an especially preferred receiving and conditioning circuit.

FIG. 4 shows the internal components of a preferred receiving circuit 61. However, it is understood that the exact construction of the receiving circuits 12 and 14 and conditioning circuits 44, 46 and 52 will depend upon the type of sensor that produces the input signal and the particular processed outputs to be derived from the signal. Nevertheless, the preferred receiving circuit 61 of FIG. 4 receives an input signal from a sensor with an input filter 62. The cutoff frequency or frequencies of input filter 62 are selected to remove any frequencies above or below the frequency range of interest that are found in the signal received from the sensor. The output of the filter 62 is supplied to an integrator 64 which integrates the signal once, twice, or not at all. Thus, an acceleration signal may be converted to a velocity signal by integrating once, or used as an acceleration signal by not integrating at all. Likewise, a acceleration signal may be converted to a displacement signal by integrating twice. The output from the integrator 64 is provided to a DC offset 66 that eliminates DC components from the signal. An amplifier 68 provides an appropriate amount of gain to raise the signal to the desired amplitude level. Finally, the signal is sent through a low pass output filter 70. The cutoff frequency of the output filter 70 is chosen so that it eliminates any extraneous high frequency components introduced into the signal without destroying any frequencies that may be indicative a machinery defect. Finally, the output of the receiving circuit 61 is sent to an analog to digital converter or microprocessor as previously discussed above.

In especially preferred embodiment, the components of the receiving circuit 61 are under the control of the microprocessor associated with the receiving circuit 61. Thus, the microprocessor controls the gain and filtering of the signal it is to receive. This allows the microprocessor to modify the conditioning of the sensor signal based upon the signal being received. An embodiment is also envisioned where a central processing unit controls the receiving circuits and their associated analog to digital converters.

While the invention has been described in detail, it is to be expressly understood that it will be apparent to persons skilled in the relevant art that the invention may be modified without departing from the spirit of the invention. Various changes of form, design or arrangement may be made to the invention without departing from the spirit and scope of the invention. Therefore, the above mentioned description is to be considered exemplary, rather than limiting, and the true scope of the invention is that defined in the following claims.

What is claimed is:

1. An apparatus for collecting and analyzing vibration data, the apparatus comprising:
   a vibration sensor for sensing vibrations and producing an electrical signal corresponding to the sensed vibrations;
   a first receiving circuit for receiving the electrical signal corresponding to the sensed vibrations from the vibration sensor and conditioning and sampling the electrical signal to produce a first conditioned signal;
   a second receiving circuit for receiving the electrical signal corresponding to the sensed vibrations from the vibration sensor and conditioning and sampling the electrical signal to produce a second conditioned signal;
   a first microprocessor for receiving the first conditioned signal and processing the first conditioned signal to produce a first processed output indicative of the presence or absence of a machinery defect; and
   a second microprocessor for receiving the second conditioned signal and processing the second conditioned signal to produce a second processed output indicative of the presence or absence of a machinery defect.

2. The apparatus of claim 1 further comprising output means for electrically receiving the first and second processed outputs from the first and second microprocessors and providing the first and second processed outputs to an external device.

3. The apparatus of claim 1 further comprising a display for providing an operator of the apparatus status information concerning the collecting and analyzing of the vibration data and displaying the first and second processed outputs.

4. The apparatus of claim 1 further comprising:
   a plurality of receiving circuits for receiving the electrical signal corresponding to the sensed vibrations from the vibration sensor and conditioning and sampling the electrical signal to produce a plurality of conditioned signals; and
   a plurality of microprocessors for receiving the plurality of conditioned signals and processing the plurality of conditioned signals to produce a plurality of processed outputs indicative of the presence or absence of machinery defects.

5. The apparatus of claim 4 further comprising a plurality of analog to digital converters for receiving the plurality of conditioned signals from the plurality of receiving circuits and sampling the plurality of conditioned signals at a plurality of different sampling rates to create a plurality of digital signals that are provided to the plurality of microprocessors.

6. The apparatus of claim 5 further comprising a central processing unit for controlling the operation of the apparatus.

7. The apparatus of claim 1 wherein the vibration sensor contains a vibration transducer that produces an electrical signal in response to vibrations.

8. The apparatus of claim 1 further comprising storage means for receiving and storing the processed outputs.

9. The apparatus of claim 1 further comprising a temperature sensor for producing a voltage signal that corresponds to the temperature of an area from which the vibration sensor is sensing vibrations.

10. A hand held vibration data collector and analyzer system for collecting, analyzing and storing vibration data that is produced by and collected from a series of machines, comprising:

a housing dimensioned and configured for being hand held by a user;

a vibration transducer for sensing vibration that is produced by the machines and producing an analog signal corresponding to the vibration;

a first conditioning circuit for receiving and conditioning the analog vibration signal from the vibration transducer to produce a first conditioned analog signal;

a second conditioning circuit for receiving and conditioning the analog vibration signal from the vibration transducer to produce a second conditioned analog signal;

a first data processor mounted in the housing for receiving and processing the first conditioned analog signal to produce a first set of desired digital data;

a second data processor mounted in the housing for receiving and processing the second conditioned analog signal to produce a second set of desired digital data;

a keyboard interfaced with the first and second data processors for inputting commands and data to the first and second data processors;

a memory interfaced with the first and second data processors for storing information; and a display interfaced with the first and second data processors for displaying information to the user.

11. The system of claim 10 wherein the first and second conditioning circuits contain analog to digital converters for sampling the first and second conditioned analog signals to produce first and second digital conditioned signals, respectively, and the first and second data processors receive the first and second conditioned digital signals.

12. The system of claim 11 wherein the analog to digital converters sample the first and second conditioned analog signals at different sampling rates.

13. The system of claim 11 wherein at least one of the first and second data processors further comprises a digital signal processor that receives one of the conditioned digital signals and performs a Fast Fourier Transform on the received conditioned digital signal to produce a frequency spectrum.

14. The system of claim 13 wherein the digital signal processor performs a rasterization operation on the frequency spectrum to generate a digitally encoded graphical representation of the frequency spectrum and transferring the digitally encoded graphical representation of the frequency spectrum to the memory.

15. The system of claim 11 wherein at least one of the first and second data processors performs a low-pass filtering and decimation operation on one of the conditioned digital signals to produce a filtered digital signal having a reduced sample rate as compared to the corresponding conditioned digital signal before decimation and is representative of a portion of the conditioned digital signal having a frequency below a selected upper frequency.

16. The system of claim 10 wherein at least one of the first and second conditioning circuits includes a fixed frequency analog anti-aliasing filter having a fixed upper cutoff frequency set at a desired frequency equal to a maximum vibration frequency of interest for producing at least one conditioned analog signal having a desired frequency range.

17. The system of claim 11 wherein the first and second conditioning circuits have amplifiers for producing the first and second digital conditioned signals at a desired amplitude.

18. The system of claim 10 further comprising a central processing unit for controlling the functioning of the hand held vibration data collector and analyzer system.

19. The system of claim 18 further comprising a direct memory access for transferring data from the first and second data processors to the memory without interrupting the functioning of the central processing unit.

20. A vibration data collector and analyzer apparatus comprising:

a single vibration sensor for producing an electrical vibration signal in response to vibrations produced by an operating machine;

at least two microprocessors for receiving the electrical vibration signal from the sensor and independently performing digital signal analysis techniques on the electrical vibration signal to produce results and examining the results to determine if the electrical vibration signal indicates that the operating machine may have a fault or defect;

an output device for receiving the results of the digital signal analysis techniques from the at least two microprocessors and providing the results of the digital signal analysis techniques to a user of the vibration data collecting and analyzing apparatus;

a memory receiving and storing the results of the digital signal analysis techniques from said at least two microprocessors; and a power supply for providing power to the vibration data collecting and analyzing apparatus.

21. A hand held data collector and analyzer system for collecting, analyzing and storing data that is produced by and collected from a series of operating machines, comprising:

a protective housing constructed out of a durable material for housing the data collector and analyzer system wherein the protective housing is dimensioned and configured for being portably held in the hands of a user;

a machine sensor mounted on the protective housing for sensing properties of operating machines and producing an analog machine sensor signal corresponding to the sensed properties of the operating machines;

a first signal conditioning circuit for receiving and conditioning the analog machine sensor signal from the machine sensor to produce a first conditioned analog machine signal;

a second signal conditioning circuit for receiving and conditioning the analog machine sensor signal from the machine sensor to produce a second conditioned analog machine signal;

a first data processor mounted in the protective housing for receiving the first conditioned analog machine signal from the first signal conditioning circuit and processing the first conditioned analog machine signal to produce a first set of desired digital machine data;

a second data processor mounted in the protective housing for receiving the second conditioned analog machine signal from the second signal conditioning circuit and processing the second conditioned analog machine signal to produce a second set of desired digital machine data;

a keyboard interfaced with the first and second data processors for inputting commands and data to the first and second data processors;

a digital memory interfaced with the first and second data processors and for storing information; and a display interfaced with the first and second data processors for visually displaying information to the user.

* * * * *